United States Patent
McIntyre et al.

(10) Patent No.: US 8,448,493 B2
(45) Date of Patent: May 28, 2013

(54) GAS CHROMATOGRAPH-COMBUSTION SYSTEM AND METHOD FOR MASS SPECTROMETRY

(75) Inventors: Cameron P. McIntyre, North Falmouth, MA (US); Sean P. Sylva, East Wareham, MA (US)

(73) Assignee: Woods Hole Oceanographic Institution, Woods Hole, MA (US)

( * ) Notice: Subject to any disclaimer, the term of this patent is extended or adjusted under 35 U.S.C. 154(b) by 556 days.

(21) Appl. No.: 12/605,152

(22) Filed: Oct. 23, 2009

(65) Prior Publication Data

US 2010/0101304 A1    Apr. 29, 2010

Related U.S. Application Data

(60) Provisional application No. 61/197,047, filed on Oct. 23, 2008.

(51) Int. Cl.
    *G01N 30/72* (2006.01)
(52) U.S. Cl.
    USPC .......................................... 73/23.37; 73/23.41
(58) Field of Classification Search
    USPC .................................. 73/23.35, 23.37, 23.41
    See application file for complete search history.

(56) References Cited

U.S. PATENT DOCUMENTS

| | | | |
|---|---|---|---|
| 3,589,171 A | 6/1971 | Haley | |
| 3,638,396 A | 2/1972 | Lovelock | |
| 4,517,461 A | 5/1985 | Crandall | |
| 4,866,270 A * | 9/1989 | Hall et al. | 250/282 |
| 5,012,052 A | 4/1991 | Hayes | |
| 5,424,539 A * | 6/1995 | Brand et al. | 250/288 |
| 5,432,344 A * | 7/1995 | Brand | 250/288 |
| 5,783,741 A * | 7/1998 | Ellis et al. | 73/23.39 |
| 6,707,035 B2 | 3/2004 | Hughey et al. | |
| 6,867,415 B2 | 3/2005 | Hughey et al. | |

FOREIGN PATENT DOCUMENTS

| | | |
|---|---|---|
| DE | 19650444 A1 | 6/1998 |
| GB | 2270977 A | 3/1994 |
| WO | WO-89/09486 A1 | 10/1989 |

OTHER PUBLICATIONS

Brand, W.,"High Precision Isotope Ratio Monitoring Techniques in Mass Spectrometry", Journal of Mass Spectrometry, vol. 31, 1996, pp. 225-235.*

Merritt, D.A. et al., "Nitrogen Isotopic Analyses by Isotope-Ratio-Monitoring Gas Chromatography/Mass Spectrometry", Journal of the American Society for Mass Spectrometry, vol. 5, Issue 5, May 1994, pp. 387-397.*

(Continued)

*Primary Examiner* — Daniel Larkin
(74) *Attorney, Agent, or Firm* — Ropes & Gray LLP

(57) ABSTRACT

A gas chromatograph-combustion apparatus and method are disclosed in which the carrier gas type and flow rate is continuously exchanged to facilitate high speed, high sensitivity compound specific isotope analysis. Samples are injected into a gas chromatograph that uses $H_2$ as the carrier gas. The gas stream exiting the gas chromatograph is passed through a combustion system in which $H_2$ and the samples are combusted, simultaneously and totally, to oxidize the sample to $CO_2$ and/or $N_2$ gas, and to convert $H_2$ gas to water vapor. Water vapor is removed using a water separator. Therefore, combustion serves the dual purpose of preparing the samples for isotopic analysis and converting $H_2$ to water vapor, which can be easily separated out. A second carrier gas may be used to convey the $CO_2$ and $N_2$ to a mass spectrometer where the isotopic composition (e.g. $^{14}C$ or $^{15}N$) is determined.

16 Claims, 9 Drawing Sheets

OTHER PUBLICATIONS

Matthews, D.E. et al., "Isotope-Ratio-Monitoring Gas Chromatography-Mass Spectrometry", Analytical Chemistry, vol. 50, No. 11, Sep. 1978, pp. 1465-1473.*

McIntyre et al., "Gas Chromatograph-Combustion System for 14C-Accelerator Mass Spectrometry," Analytical Chemistry, 81:15, Jul. 2009, pp. 6422-6428.

Meier-Augenstein, W., "Applied gas chromatography coupled to isotope ratio mass spectrometry," Journal of Chromatography, 842:1-2 (May 21, 1999), pp. 351-371.

Ramsey et al., "Using a Gas Ion Source for Radiocarbon AMS and GC-AMS," Radiocarbon, 46:1, 2004, pp. 25-32.

Skipper et al., "Bringing AMS into the bioanalytical chemistry lab," Nuclear Instruments & Methods in Physics Research, Section—B: Beam Interactions with Materials and Atoms, 223-224, Aug. 1, 2004, pp. 740-744.

ISR and Written Opinion issued Apr. 22, 2010 for PCT/US2009/061912.

McFadden, W. H., "Techniques of combined gas chromatography/mass spectrometry: Applications in organic analysis," John Wiley and Sons: New York, 1973, pp. 157-221.

Simmonds, P. G., et al, "Palladium-Hydrogen System—Efficient Interface for Gas Chromatography-Mass Spectrometry," Analytical Chemistry, 42:8, Jul. 1970, pp. 881-885.

Lovelock, J. E., et al, "The Palladium Transmodulator: A New Component for the Gas Chromatograph," Analytical Chemistry, 41:8, Jul. 1969 pp. 1048-1052.

* cited by examiner

GAS CHROMATOGRAPH-COMBUSTION SYSTEM AND METHOD FOR MASS SPECTROMETRY

CROSS-REFERENCE TO RELATED APPLICATIONS

This application claims the benefit of U.S. Provisional Patent Application No. 61/197,047, entitled "Gas Chromatograph-Combustion System and Method for Mass Spectrometry" filed on Oct. 23, 2008, the entire disclosure of which is hereby incorporated by reference as if set forth herein in its entirety.

FIELD OF THE INVENTION

Generally, the systems and methods described herein relate to performing compound specific isotopic and chemical analysis. More specifically, the systems and methods described herein relate to the preparation of samples for radiocarbon analysis with a gas accelerator mass spectrometer (AMS) or isotope ratio mass spectrometer (IRMS).

BACKGROUND

It is has been established for some time that isotopic analysis of compounds provides additional information extending beyond traditional structural and chemical analyses. While quantitative and qualitative structural analyses identify the chemical composition or structure of individual compounds, isotopic composition provides still further information concerning the origin, cycling and fate of these compounds.

In sports drug testing, compounds such as the steroid hormone testosterone are screened for, identified and quantified using conventional analytical techniques. The origin of the hormone is confirmed using $^{13}C$ isotope measurements that discriminate between the endogenously produced compound, and an illegally administered synthetic equivalent.

There are further applications in ecology where the stable C, N, and S isotopic compositions of biota are used to determine the relative trophic positions of major organisms and examine the spatial and temporal changes in food web structures across ecosystems. This is especially important with respect to the effect on food webs of anthropogenically derived nutrients and contaminants from agricultural land uses.

Additional applications lie in oil exploration and oil spill identification where the isotopic compositions of large numbers of compounds from various oil samples and reservoirs are used to correlate compounds to their source. In exploration this can assist in understanding petroleum generation and migration which can be used to locate other reservoirs. In oil spill identification (and with other environmental pollutants) several potential sources may exist. Isotopic compositions of a select set of compounds can identify a single source or, in the case that an intermediate isotopic value is obtained, be used for source apportionment.

In addition to stable isotopes there are radioisotopes such as $^{14}C$ (radiocarbon), which forms naturally in the atmosphere at very low abundances due collisions between nitrogen gas and comic rays. Radiocarbon exists in $CO_2$ gas and is taken up by biological organisms (e.g. plants) or anything else that uses or adsorbs $CO_2$. Materials enriched with radiocarbon are also produced artificially by man in laboratories or, in the case nuclear weapons testing, from radioactive residues. The half-life of $^{14}C$ is approximately 5700 years which imparts a useful characteristic in that it can be used for age dating of carbon containing materials. At natural abundance levels this is widely applied in archeology for ages up to 60,000 years. Biomedical research uses $^{14}C$ enriched compounds as a tracer label to study drug metabolism. The low natural abundance of radiocarbon makes it easier to identify labeled metabolites and study the fate of drugs in an organism however, labeled compounds and the analysis techniques employed are often costly. Methods and apparatus that improve the speed, sensitivity and precision of compound specific $^{14}C$ analysis may minimize the amount labeled sample required and enhance applications in the biomedical field. This also applies to natural abundance levels of radiocarbon, stable isotopes and their respective applications.

Compound specific isotope analysis is typically achieved using a combination of gas chromatography (GC) to separate individual compounds, and mass spectrometry to determine isotopic composition of each compound. Stable isotopes such as $^{13}C$, $^{15}N$, $^{2}H$ and $^{34}S$ are routinely analyzed using an isotope-ratio mass spectrometer (IRMS) system. Radioactive isotopes such as $^{14}C$ that occurs in very low abundances (around one part in a trillion) require a specialized and selective accelerator mass spectrometry (AMS) system. Compound separation and isotope analysis can be performed either "offline" where components are separated, collected and analyzed individually or "online" where the two systems are connected and analytes flow continuously from one to the other. The benefits of online analysis include: faster analysis times, reduced labor requirements, and increased sensitivity and precision resulting from the direct delivery of smaller amounts of analytes from the gas chromatograph to mass spectrometer.

However, matching a gas chromatograph to a mass spectrometer system for online isotope analysis presents a significant technical challenge. In particular, it may be necessary to combine two individual systems that function well separately with an interface. Both have optimum operating conditions that are not always compatible. Specifically, the carrier gas used to optimally transmit the analytes through each system may be different, and generally, may not match in flow rate. For example, the carrier gas used in a gas chromatograph may be hydrogen or helium, whereas the carrier gas for an AMS system may be Argon. Moreover, a gas chromatograph may supply compounds that are intact whereas, for high precision isotope measurements, AMS and IRMS systems may be configured to accept analytes as $CO_2$ or $N_2$ gas. Although, scientists have developed systems for interfacing a gas chromatograph with conventional mass spectrometers, these systems do not work well when used in conjunction with an AMS or IRMS system. For example, scientists use palladium tubing/membranes to separate out hydrogen, which is often the carrier gas for a chromatograph. However, palladium tubing poses several problems including absorbing some of the analyte and thereby diminishing sample output.

Accordingly, there is a general need for systems and methods for performing compound specific isotopic and chemical analysis. More specifically, there is a need for apparatus and methods for interfacing a gas chromatograph with mass spectrometers, and for preparing samples for AMS and IRMS systems.

SUMMARY

The systems and methods described herein are directed to methods and systems for preparing a sample for mass spectrometry. In particular, a gas chromatograph-combustion apparatus and method are disclosed in which the carrier gas type and flow rate is continuously exchanged to facilitate high speed, high sensitivity compound specific isotope analysis. Samples are injected into a gas chromatograph that uses $H_2$ as the carrier gas. The gas stream exiting the gas chromatograph is passed through a combustion system in which $H_2$ and the samples are combusted, both simultaneously and totally, to oxidize together the sample to $CO_2$ and/or $N_2$ gas (depending at least on the sample), and to convert $H_2$ gas to water vapor. Water vapor is removed using a water separator. Therefore, combustion serves the dual-purpose of simultaneously preparing the samples for isotopic analysis and converting $H_2$ to water vapor, which can be easily separated out. A second carrier gas may be used to convey the $CO_2$ and $N_2$ to a mass spectrometer where the isotopic composition (e.g. $^{14}C$ or $^{15}N$) is determined.

For purposes of clarity, and not by way of limitation, the systems and methods may be described herein in the context of preparing a sample for mass spectrometry. Also, the systems and methods may be decribed herein in the context of interfacing a gas chromatograph with an AMS or IRMS system. However, it may be understood that the systems and methods described herein may be applied to provide for preparing a sample suitable for other types of chemical analyses. It may be further understood that the systems and methods described herein may be applied to interfacing any other suitable system for converting a sample into discrete compounds or components, with any detector, or any mass spectrometer without departing from the scope of the invention. The systems and methods described herein may be applied to performing isotopic analysis for measuring quantities of stable isotopes and/or radio isotopes using any detectors. The systems and methods described herein may also be applied to performing any quantitative or qualitative chemical analysis using any detectors such as thermal conductivity detectors, optical detectors, chemical detectors, and electrical detectors.

In the radiocarbon analysis of organic substances, gas chromatography may be employed to separate a sample into discrete components prior to analyzing using accelerator mass spectrometer (AMS). In the case of stable isotopes, an isotope radio mass spectrometer (IRMS) may be used). To perform gas chromatography, a sample and a carrier gas may be introduced via an inlet into a column where the sample separates into discrete components as it passes through. A gas stream exits the column and the components may be detected with a suitable detector such as gas accepting accelerator mass spectrometry system for radiocarbon analysis. In the case of gas accepting accelerator mass spectrometry systems, the gas stream from the gas chromatograph may be analyzed directly (on-line).

In one aspect, the disclosure relates to a method of sample preparation that subtantially or totally removes a hydrogen carrier gas from the output of the gas chromatograph using only combustion and a water separator instead of selective permeation of hydrogen through a separator, such as a palladium membrane. Continuous exchange of the carrier gas may allow gas chromatograph to be matched to the mass spectrometer, thus improving sensitivity. The use of hydrogen carrier gas may improve chromatographic performance and reduces analysis time.

In some embodiments, the method for sample preparation comprises injecting an organic sample into a hydrogen carrier gas passing into a chromatograph, separating the organic sample into discrete components, mixing the resulting gas stream with oxygen and a make up gas to produce a gas mixture, passing the gas mixture into a combustion system, combusting the hydrogen carrier gas and sample completely, producing carbon dioxide, water vapor and make up gas, and removing the water vapor using a water separator, resulting in a concentrated sample in gas suitable for accelerator mass spectrometry. In certain embodiments, the sample is suitable for isotope radio mass spectrometer.

In one aspect, the disclosure relates to a method for combusting microgram quantities of an organic sample and exchanging the resulting $CO_2$ from a high gas flow rate at the output of the gas chromatograph to a low flow rate of a gas suitable for accelerator mass spectrometry. Even though the flow rate of the hydrogen carrier for gas chromatography is high (typically up to about 15 ml/min), the low flow rate (less than about 1 ml/min) for accelerator mass spectrometry may be achieved by controlling the flow rate of the make up gas and the ratios of hydrogen to oxygen in the combustion system. By combusting the hydrogen carrier and samples completely, or substantially completely, the combustion system produces water vapor as the main by-product of the combustion process. The by-product, water vapor, may be removed later by a water separator to produce a concentrated sample of $CO_2$ gas and/or $N_2$ gas in the make up gas.

In certain embodiments, the system for sample preparation comprises an organic compound as sample, a gas chromatograph fitted or retrofitted with a hydrogen source, an oxygen source, a make up gas source, combustion system, a water separator, temperature controllers for the furnace, water separator and pressure regulators, and valves for controlling gas flows.

In some embodiments, the system is an interface that connects a gas chromatograph to a mass spectrometer. The gas chromatograph may be used to separate samples into individual compounds and the mass spectrometer may be used to measure isotopic composition. The system may simultaneously combust the compounds and carrier gas (hydrogen) eluting from the gas chromatograph and selectively remove the combustion product of the carrier gas (water) with a drying apparatus (water separator). Addition of a second carrier gas may convey the combustion products of the sample ($CO_2$ and/or $N_2$) to the mass spectrometer. The mass spectrometer may be an accelerator mass spectrometer for $^{14}C$ analysis or a isotope ratio mass spectrometer for stable isotopes such as $^{13}C$, $^{15}N$, $^{2}H$ or $^{34}S$. The mass spectrometer may be any suitable device suitable for analyzing stable isotopes and/or radio isotopes without departing from the scope of the invention. In certain embodiments, the system combusts the separated compounds so they have the correct chemical composition for high precision isotopic measurements.

The system may enable the type of carrier gas to be exchanged and the flow rate of the carrier gases to adjusted independently so that the gas chromatograph and mass spectrometer may be precisely matched. Matching of the gas flows may provide a greater proportion of the sample reaching the mass spectrometer, thereby boosting sensitivity and precision. The use of hydrogen carrier gas may improve chromatographic performance and reduces analysis time. A portion of the gas stream may be directed to secondary detectors located at the outlet of the gas chromatograph or the drying apparatus so the intermediate composition of the gas stream may be determined. A backflush valve may be used to divert the solvent (of the sample) to a vent before reaching the combustion system to prevent a reduction of combustion performance.

In one embodiment, a sample may be analyzed. Samples and a hydrogen carrier gas may be injected into a gas chromatograph. Samples may be separated into a plurality of compounds to produce an output gas stream from the gas chromatograph. The output gas stream from the gas chromatograph may be mixed with oxygen gas and an inert carrier gas suitable for a mass spectrometer to produce an input gas stream for the combustion system. The hydrogen carrier gas in the input gas stream gas stream of the combustion system may be combusted, substantially completely, to produce an output gas stream for the combustion system, wherein the output gas stream of the combustion system may include the inert carrier gas, carbon dioxide gas, and water vapor. The water vapor from the output gas stream of the combustion system may be substantially removed using a water separator to produce a gas stream for analysis, wherein the gas stream for analysis comprises inert carrier gas and carbon dioxide gas. The gas stream for analysis may be provided to the mass spectrometer fitted with a gas ion source.

In one aspect of the invention, the mass spectrometer may include at least one of an isotope ratio mass spectrometer and an accelerator mass spectrometer. In another aspect of the invention, mixing the output gas stream from the gas chromatograph with oxygen gas may comprise providing an amount of oxygen gas at substantially the stoiciometric ratio of 2:1 with the hydrogen carrier gas to allow for combustion to occur substantially completely. In yet another aspect of the invention, combusting at least one of the hydrogen carrier gas and the sample in the input gas stream of the combustion system may comprise using metal and metal oxides as a catalyst.

In one aspect of the invention, the output gas stream of the combustion system may further includes nitrogen gas, and the gas stream for analysis further includes nitrogen gas. In certain embodiments, the output gas stream of the combustion system may further include oxides of nitrogen, and the gas stream for analysis may further include oxides of nitrogen. Oxides of nitrogen may include at least one of NO, $NO_2$ and $N_2O$. Other oxides of nitrogen may also be included. The nitrogen oxide in the gas stream for analysis may be substantially removed in a reduction furnace to reduce nitrogen oxide into nitrogen gas. According to one aspect of the invention the inert carrier gas may be helium gas or argon gas. In some embodiments, separating samples into a plurality of compounds may include separating into a one or more components, each component having one or more compounds.

In one embodiment, a sample may be analyzed. Samples, an inert carrier gas, and a hydrogen carrier gas may be injected into a gas chromatograph, wherein the inert carrier gas may be suitable for a mass spectrometer fitted with a gas ion source. Samples may be separated into a plurality of compounds to produce an output gas stream from the gas chromatograph. The output gas stream from the gas chromatograph may be mixed with oxygen gas to produce an input gas stream for the combustion system. The hydrogen carrier gas in the input gas stream gas stream of the combustion system may be combusted, substantially completely, to produce an output gas stream for the combustion system, wherein the output gas stream of the combustion system includes the inert carrier gas, carbon dioxide gas, and water vapor. The water vapor from the output gas stream of the combustion system may be substantially removed using a water separator to produce a gas stream for analysis, wherein the gas stream for analysis may comprises inert carrier gas and carbon dioxide gas. The gas stream for analysis may be provided to the mass spectrometer fitted with a gas ion source. In one aspect of the invention, separating samples into a plurality of compounds may include separating into a one or more components, each component having one or more compounds.

In one embodiment, a gas chromatograph may be interfaced with a mass spectrometer. Samples and a hydrogen carrier gas may be injected into a gas chromatograph, wherein the hydrogen carrier gas may have a flow rate suitable for gas chromatography. Samples may be separated into a plurality of compounds using the gas chromatograph to produce a first gas stream. The first gas stream may be mixed with oxygen gas and an inert carrier gas to form a second gas stream, wherein the inert carrier gas may have a flow rate suitable for mass spectrometry. The hydrogen carrier gas in the first gas stream may be combusted substantially completely to produce a second gas stream to remove the hydrogen carrier gas while the inert carrier gas remains, wherein the second gas stream comprises the inert carrier gas and combustion products. Water vapor from the second gas stream may be substantially removed to form a third gas stream. The third gas stream may be provided to a gas ion source.

According to one aspect of the invention, the flow rate suitable for gas chromatography is about 1 to about 100 milliliters per minute. In some embodiments, the flow rate suitable for gas chromatography is about 1 to about 10 milliliters per minute. According to another aspect of the invention, the flow rate suitable for mass spectrometry is about 0.001 to about 1.0 milliliters per minute. In some embodiments, the flow rate suitable for mass spectrometry is about 0.2 to about 1.0 milliliters per minute.

According to another aspect of the invention, the gas ion source may be at least one of a microwave plasma ion source and an electron ionization source. In one aspect of the invention, separating samples into a plurality of compounds may include separating into a one or more components, each component having one or more compounds.

In one embodiment, a sample may be prepared for mass spectrometry. Gas mixture may be provided to a combustion system, wherein the gas mixture may comprise a sample, a hydrogen carrier gas and an inert carrier gas. Sufficient oxygen gas may be provided to the combustion system to convert the compound into carbon dioxide gas and combust substantially all the hydrogen carrier gas into water. The water may be substantially removed using a water separator to produce a gas mixture where carbon dioxide gas and the inert carrier gas remains. The remaining carbon dioxide gas and the inert carrier gas may be provided to a mass spectrometer fitted with a gas ion source. In certain embodiments, separating samples into a plurality of compounds may include separating into a one or more components, each component having one or more compounds.

In one embodiment, an online system for isotopic analysis is provided. A sample may be separated into discrete compounds. One of the discrete components and a carrier gas suitable for separating the sample may be directed to a combustion system. An inert carrier gas and oxygen gas may be introduced to the combustion system, wherein the second carrier gas may be inert and suitable for a mass spectrometer. The carrier gas used for separating the sample may be removed substantially completely by combustion to form a mixture of combustion products carried by the inert carrier gas. Combustion products that are not suitable for mass spectrometry may be removed. The remaining combustion products and the inert second carrier gas may be directed to the mass spectrometer fitted with a gas ion source.

According to one aspect of the invention, separating the sample into discrete compounds may comprise mixing a sample with a carrier gas suitable for separating the sample and providing the sample and the carrier gas suitable for separating the sample to a gas chromatograph to separate the sample into discrete components.

In one aspect of the invention, combustion products may comprise carbon dioxide gas and water vapor. In another aspect of the invention, Removing combustion products that are not suitable for mass spectrometry may include substantially removing water vapor generated from the combustion using a water separator. In yet another aspect of the invention, separating the sample into discrete compounds may include separating into a one or more components, each component having one or more compounds.

BRIEF DESCRIPTION OF THE FIGURES

The foregoing and other objects and advantages of the invention will be appreciated more fully from the following further description thereof, with reference to the accompanying drawings wherein.

DETAILED DESCRIPTION OF THE FIGURES

To provide an overall understanding of the invention, certain illustrative embodiments will now be described, including systems and methods for preparing a sample for mass spectrometry, such as accelerator mass spectrometry and isotope radio mass spectrometry. However, it will be understood by one of ordinary skill in the art that the systems and methods described herein may be adapted and modified for other suitable applications and that such other additions and modifications will not depart from the scope thereof.

The systems and methods described herein include, among other things, systems and methods for analyzing samples. Samples are injected into a gas chromatograph that uses $H_2$ as the carrier gas. The gas stream exiting the gas chromatograph is passed through a combustion system in which $H_2$ and the samples are combusted, simultaneously and totally, to oxidize the sample to $CO_2$ and/or $N_2$ gas, and to convert $H_2$ gas to water vapor. Water vapor is removed using a water separator. Therefore, combustion serves the dual purpose of preparing the samples for isotopic analysis and converting $H_2$ to water vapor, which can be easily separated out. A second carrier gas may be used to convey the $CO_2$ and $N_2$ to a mass spectrometer where the isotopic composition (e.g. $^{14}C$ or $^{15}N$) is determined.

Figure 1:
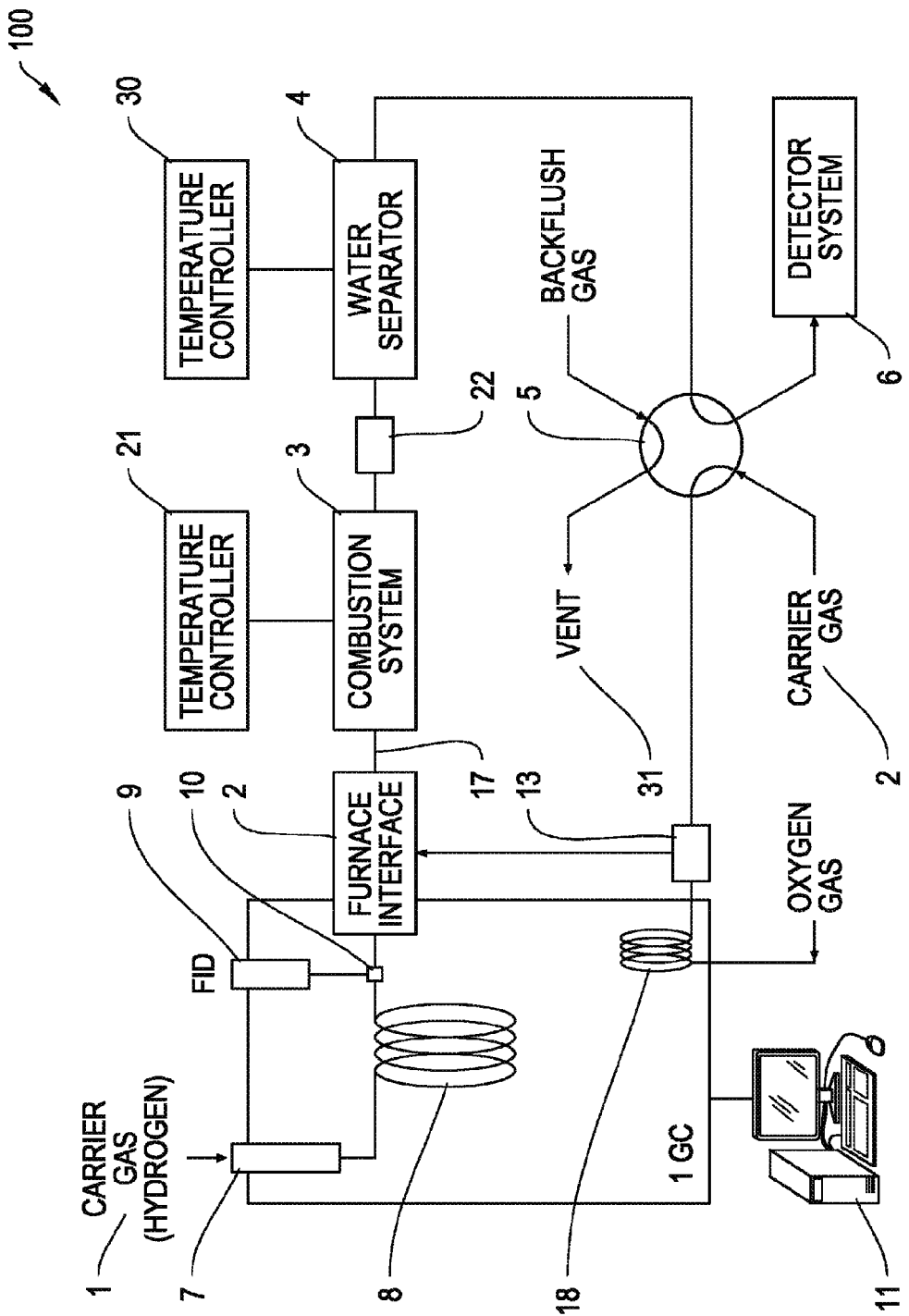
FIG. 1 depicts a gas chromatograph-combustion system, according to an illustrative embodiment of the invention.

In particular, FIG. 1 depicts a system 100 for carrying out the gas chromatograph-combustion method. System 100 includes gas chromatograph 1, furnace interface 2, combustion system 3, water separator 4, backflush valve 5 and detector system 6. Ferrules (not shown) used throughout system 100 may be made from graphitized vespel or any other suitable material that provides heat resistance, dimensional stability, chemical resistance, and creep resistance.

System 100 may include gas chromatograph 1, which may be configured to separate samples into discrete components. A gas chromatograph, such as gas chromatograph 1, typically uses about 1 to about 100 ml/min hydrogen or helium as a carrier gas for optimal performance. In some embodiments, a gas chromatograph may use about 1 to about 10 ml/min hydrogen or helium as a carrier gas for optimal performance. Any suitable carrier gas, may be used as primary carrier gas for the gas chromatograph. The flow rate may be determined by the length and diameter of the capillary column used for separation, the gas type and operating temperature. Compounds may interact with a specific film on the inside of the capillary column and may be separated by volatility and polarity as they pass through. The compounds may elute from the capillary column at atmospheric pressure as intact molecules in the carrier gas. When a gradient temperature program is used for particular separation, then the gas flow through the instrument may slow over the course of a run due to an increase in gas viscosity. A constant flow may be maintained by electronically controlling the gas pressure. A conventional gas chromatograph may be used for gas chromatograph 1. For example, gas chromatograph 1 may include an HP5890 Series II gas chromatograph manufactured by Hewlett-Packard, Avondale, Pa., USA.

Gas chromatograph 1 may include injector 7, column 8, and detector 9. Injector 7 may serve as an inlet and be configured to allow for the injection of the sample and carrier gas suitable for gas chromatograph 1 into column 8. For instance, injector 7 may be an on-column capillary inlet or a programmed temperature vaporizing (PTV) injector to minimize isotopic fraction. Column 8 may include an open tube capillary column that may be used to enhance resolution, reduce column bleed and reduce analysis time. Low column bleed may reduce the background signal for isotopic measurements and higher resolution increases the time between separated compounds. Column 8 may include a 60 m, Restek Rxi-1 ms, 0.53 mm i.d., 1.5 film thickness, megabore capillary column manufactured by Restek, Bellefonte, Pa., USA.

Detector 9 may be coupled to the end of column 8, and may be employed to monitor the chromatographic effluent of column 8. Detector 9 may be of any type, for instance, a flame ionization detector (FID) may be employed. An FID may be preferable for detecting a wide range of compounds. An FID may be very sensitive and its response tends to be linear across a wide range of concentrations. In some embodiments, hydrogen gas (as a carrier gas, labeled as carrier gas 1) carries the sample through column 8. The effluent from column 8 in gas chromatograph 1 may be divided via passive split 10 between detector 9 and interface 2. The detector 9 may be used to determine the abundance of individual compounds in the sample. Detector 9 may be further useful to monitor system performance, but may be optional, and may be removable if greater sensitivity is desired.

The monitoring (by detector 9) of the effluent from column 8 may be recorded by data system 11. Data system 11 may be a processor system such as a personal computer, or any suitable stand-alone system or a system connected to a network, for recording and managing of the data produced by detector 9. Data system 11 may include, among other things, a user input device, memory, display, processor, and network interface. A user input device may be configured to allow users to control data system 11. Memory, such as a hard disk, removable disk, RAM, flash memory, may be used to store data produced by detector 9, or produced by gas chromatograph 1. A display such as an LCD screen or any other suitable display may be used by the operator of the system to view information about data system 11 or data recorded by detector 9. The processor, such as a microprocessor, may be used to control various devices in data system 11 or perform any necessary computations. A network interface may be used to send the data recorded by detector 9 or any other information to other systems connected to a network.

The gas chromatograph 1 may be used to separate a sample into individual compounds prior to further purification and analysis. Operating parameters of gas chromatograph 1 may be configured on gas chromatograph 1 or on data system 11 to maximize the resolution of the peaks. Co-elution of peaks may not be desirable as this may cause isotopic measurements to be less precise. Gas chromatograph 1 may be substituted with other systems that resolve samples to discrete components. For instance, a programmable temperature pyrolysis apparatus in which samples are subjected to pyrolysis in a stream of hydrogen prior to combustion may be used. In certain embodiments, the resolution of mixed components may not be required and the gas chromatograph 1 may be substituted with a gas handling system.

In certain embodiments, carrier gas pressure in the gas chromatograph 1 was set to give an average linear velocity of about 49 cm/s at about 30° C. (about 7.6 mL/min) for $H_2$. In such embodiments, He gas may be used for standby, purging and conditioning purposes. The temperature of the gas chromatograph oven was programmed from about 30° C. to about 90° C. at about 25° C./min, from about 90° C. to about 320° C. at about 10° C./min, and held at about 320° C. for about 20 min. In certain embodiments, the gas chromatograph 1 may be operated in a substantially constant pressure mode with the temperature of the injector set to track that of the oven, and gas chromatograph furnace interface 2 may be held at about 300° C. The gas chromatograph may be retrofitted with one, two or more temperature controllers, solid state relays, and K-type thermocouples manufactured by Omega, Stamford, Conn., USA.

The primary effluent of gas chromatograph 1 may be directed into furnace interface 2, which is a component of the interface system. Furnace interface 2 is discussed at length in relation to FIG. 3. Additional gases may be introduced to the gas stream at furnace interface 2.

The additional gases may include a carrier gas (labeled as carrier gas 2) suitable for detector system 6, and oxygen for combustion system 3. In some embodiments, more hydrogen gas is introduced at furnace interface 2. In certain embodiments, detector system 6 is a mass spectrometer for measuring isotope composition such as an accelerator mass spectrometer or isotopic ratio mass spectrometer. Suitable gases for such systems may be inert gases such as argon or helium. The carrier gas suitable for detector system 6 is preferably introduced at a flow rate suitable for detector system 6 and to move the analytes through the interface without significant post-column broadening of the peaks. For an accelerator mass spectrometer or isotopic ratio mass spectrometer, the carrier gas flow rate is typically between about 0.001 and about 1.0 mL/min. In some embodiments, the carrier gas flow rate for an accelerator mass spectrometer may be between about 0.2 and about 1.0 mL/min.

Figure 3:
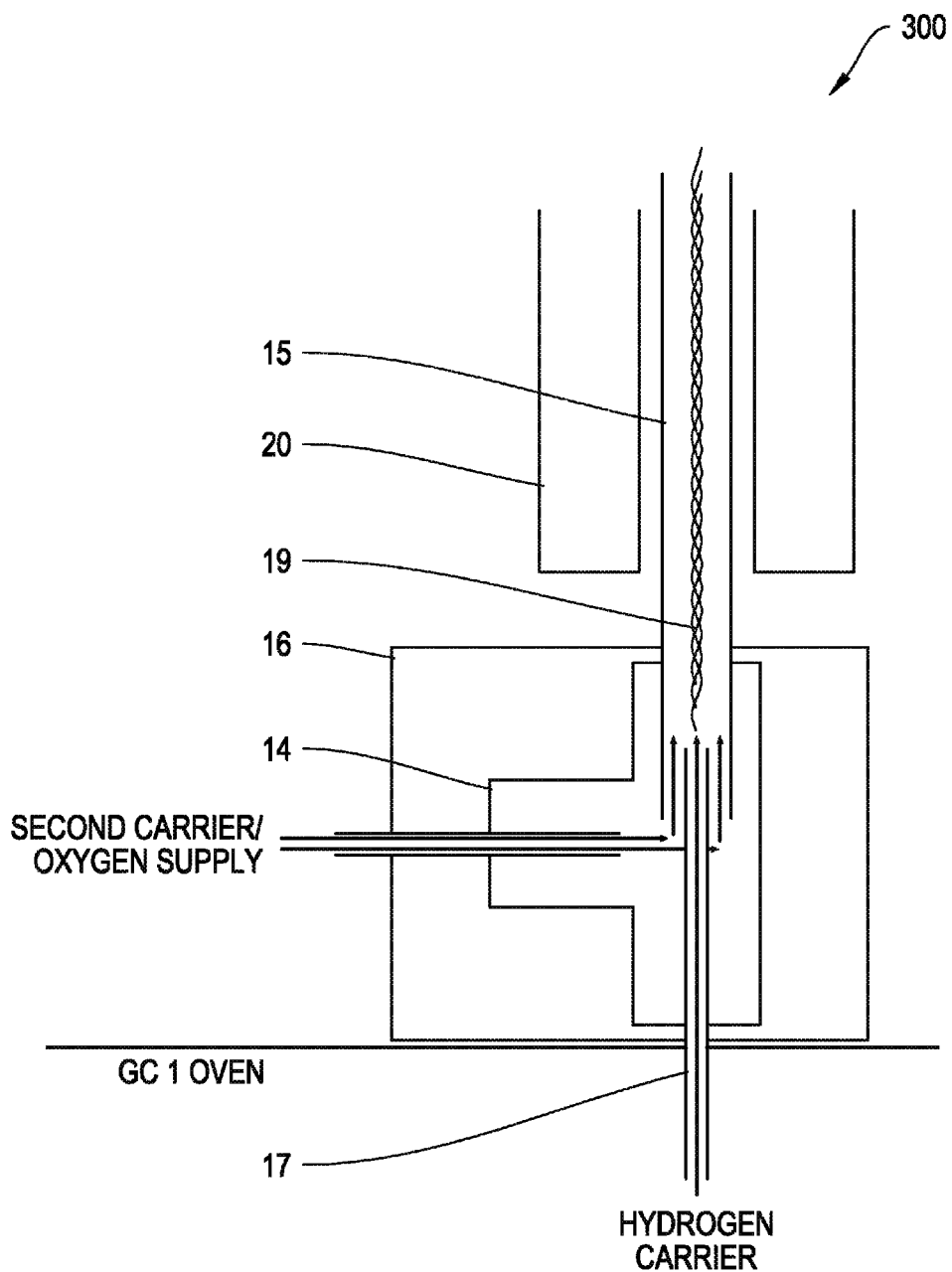
FIG. 3 depicts a furnace interface of the gas chromatograph-combustion system of FIG. 1, according to an illustrative embodiment of the invention.

Furnace interface 2 may be located such that the entrance is inside the oven of gas chromatograph 1 and the external portion is in heated block 16 (shown in FIG. 3). Returning to FIG. 1, such a configuration ensures that few or no cold spots exist and that compounds are transmitted efficiently to combustion system 3 in the vapor phase. Carrier gas 2 and/or oxygen gas may be delivered to the system using pressure regulators and capillaries (e.g., capillary 18). The gasses may be mixed with tee 13 prior to admission to furnace interface 2.

In some embodiments, an accelerator mass spectrometry system or isotope ratio mass spectrometer may be used for detector 6. Such systems used for determining isotope composition may be vacuum systems and draw in carrier gas into an ion source via a capillary tube that may act as an entrance and restrictor. Stability and precision requires that a constant high vacuum is maintained which thereby limits the flow rate that can be accepted by detector 6. In typical isotope ratio mass spectrometers, helium at a flow rate of approximately 0.2 to approximately 0.3 mL/min is the preferred operating condition. Higher flow rates may degrade performance due to factors such as a build-up of space-charge in the ion source which decreases beam quality. Lower flow rates may limit the sample size and the resulting sensitivity.

Oxygen gas for combustion may flow through capillary 18 located in the oven of gas chromatograph 1. Capillary 18 may be configured to pass through the oven of gas chromatograph 1 so that change in oxygen viscosity with temperature is substantially proportional to that of the hydrogen carrier gas. As a gas is heated, it becomes more viscous, and its flow rate slows through a tube of fixed dimensions. If gas chromatograph 1 is operated in constant pressure mode (i.e., the pressure of the hydrogen carrier gas or any suitable carrier gas 1 is held constant at injector 7), the increase in temperature of the oven in gas chromatograph 1 may result in the flow rate of the hydrogen gas. Typically, an analytical run with a gas chromatograph employs a gradient temperature program in constant temperature mode. As a consequence, the flow rate of carrier gas may decrease as the run progresses. For quantitative combustion of the gas chromatograph effluent, hydrogen and oxygen is preferably maintained close to the stoichiometric ratio of about 2:1. Thus, passing capillary 18 of the oxygen supply through the oven of gas chromatograph 1 exposes the oxygen to the same temperature changes as the hydrogen carrier gas. The change in viscosity with temperature of hydrogen and oxygen may not be equal but sufficiently close such that the configuration may be adequate to maintain the stoichiometric ratio of the gases close to about 2:1. The catalyst wire 19 used in the reactor tube 15 (both shown in FIG. 3) may supply additional oxygen to combustion system 3 to make up for any deficit that may occur. Capillary column 17 may be used to connect furnace interface 2 to combustion system 3.

In alternative embodiments, carrier gas 2 (for detector system 6) may be introduced with carrier gas 1 (e.g., hydrogen gas) at injector 7. A single gas supply such as 10% helium in hydrogen may be used, or two separate (helium and hydrogen) supplies may be mixed at a tee prior to injection. The flow rates may be controlled using electronic pressure controllers. In certain embodiments, oxygen may be introduced at the end of capillary column 17 prior to combustion.

Combustion system 3 may be configured to convert the compounds of interest into carbon dioxide for isotopic composition measurements and, combust the hydrogen carrier gas to water. Details about combustion system 3 is discussed at length in relation to FIG. 3. In some embodiments, the output of combustion system 3 further includes nitrogen gas. In some embodiments, the output of combustion system 3 further includes $SO_2$ gas for isotopic analysis of $^{34}S$. Combustion system 3 is further coupled with temperature controller 21 for monitoring and controlling the temperature inside combustion system 3.

From combustion system 3, the output gas stream passes via union 22 to water separator 4. Union 22 and connecting tubing is maintained at a temperature greater than 100 degrees Celsius to ensure water stays in the vapor state. If water condenses in this region, it might block the flow path. Heat may be applied by any suitable means. In certain embodiments, radiant heat from combustion system 3 is used, specifically furnace 20 (shown in FIG. 3). Union 22 may be shielded by an insulating blanket such that heat emanating from furnace 20 passes over the connecting tubing and union 22. An aluminum block fitted with a heater cartridge may also be suitable. Water separator 4 may be configured to remove water generated during combustion from the gas stream effluent from union 22. Details regarding water separator is discussed at length in relation to FIG. 4. Water separator 4 is further coupled with temperature controller 30 for monitoring and controlling the temperature inside water separator 4.

Once the gas stream exits water separator 4, the gas stream may pass to detector system 6. Radioisotopes such as $^{14}C$ may be measured with an accelerator mass spectrometry system fitted with a gas ion source. Stable isotopes such as $^{13}C$, $^{15}N$, $^{34}S$ may be measured with a conventional isotope ratio mass spectrometer. The ion source of the mass spectrometer may be held under vacuum and a length of capillary may used as an entrance and restrictor. The size of the capillary may determine the flow rate gas delivered to the source. A substantially constant flow rate of gas may be necessary to maintain a stable ion beam for precise isotopic compositions.

Gas accepting ion sources may be configured to accept carbon dioxide gas directly to facilitate analyses and decrease sample size. Samples may be analyzed directly as carbon dioxide and analysis time may be substantially reduced. For instance, a microwave plasma ion source may be used. Within the ion source, an argon plasma may be generated using 2.45 GHz microwaves and may be contained by a magnetic field. Sample carbon dioxide gas may be introduced with argon carrier gas via a capillary where the sample carbon dioxide may be ionized in the plasma. An ion beam may be extracted and injected into the mass spectrometer system for $^{14}C$ analysis. Gas may be continuously flowing and the system may have a minimal memory due to the absence of sputtering. The sample requirements of an accelerator mass spectrometer for $^{14}C$ measurements at natural abundance levels to attain the precision of hybrid source systems are a minimum of about 2 μg of carbon in a flow of about 0.2 to about 0.5 mL/min argon gas.

An open split may be used between the interface system (includes, among other things, furnace interface 2, combustion system 3 and water separator 4) and detector system 6. The open split may function to match the flow rates of the two systems, permit introduction of reference gas for calibration, and to provide a sampling point for a residual gas analyzer. The mass spectrometer may draw in gas from the interface system via the open split. When the gas is less than the amount supplied by the GC interface system, the remainder may be vented to the atmosphere at the open split. When more gas is withdrawn than what is supplied by the interface system, the difference may be made up by a gas purging the open split. The gas purging the open split may be the same the gas for the mass spectrometer. A reference gas may be used for calibration of the mass spectrometer and may be introduced at the open split. A capillary supplying reference gas with a known isotopic is actuated into the gas stream at regular intervals and bracketing the peaks of interest. A residual gas analyzer may be used to monitor the composition of the gas stream at the open split so that optimum performance can be tuned. Specifically, a residual gas analyzer may be used to monitor and minimize the oxygen level in the gas stream.

Figure 2:
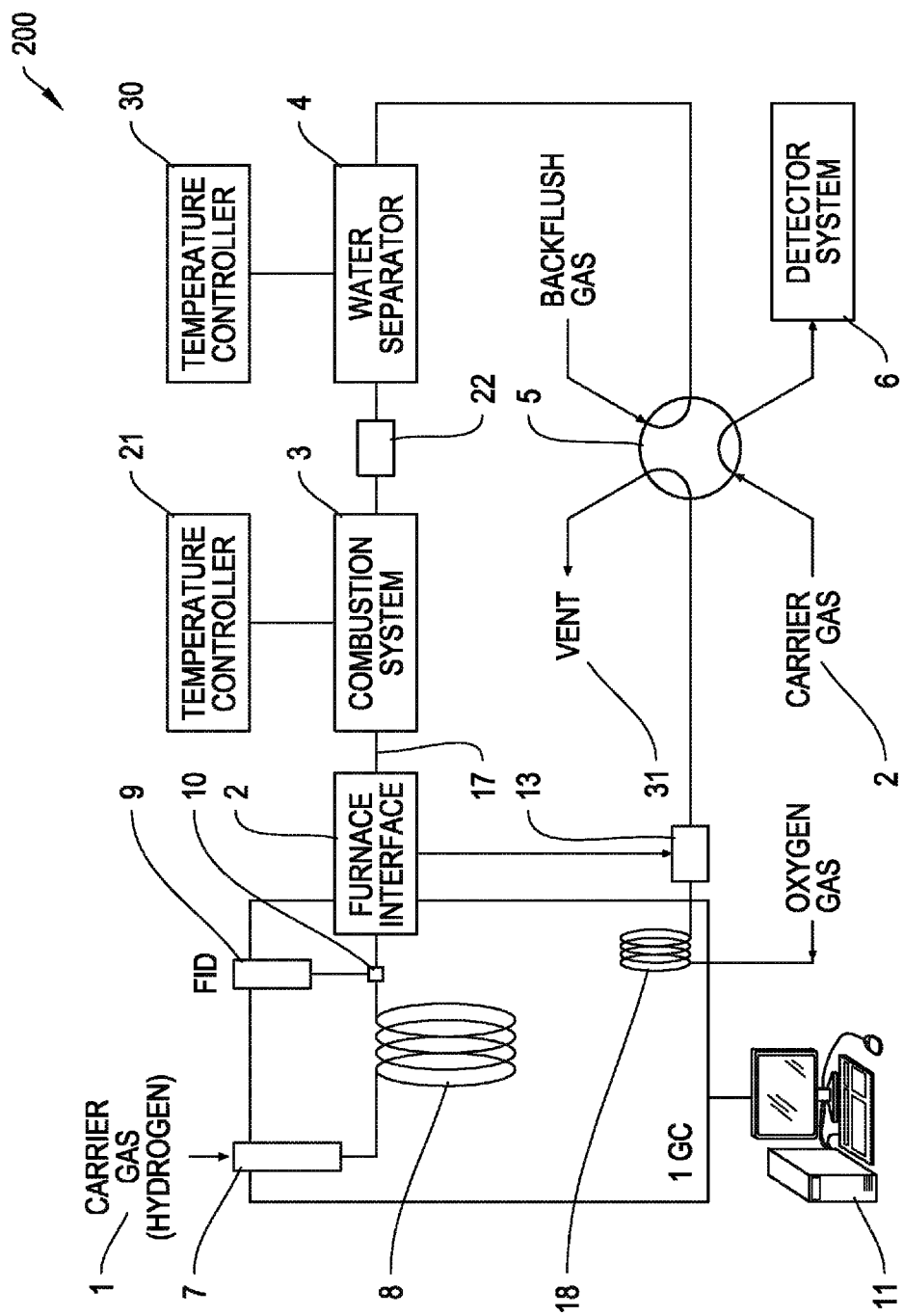
FIG. 2 depicts a gas chromatograph-combustion system of FIG. 1 in a backflush configuration, according to an illustrative embodiment of the invention.

A backflush valve 5 may be used to direct unwanted components of the sample to vent 31. In this embodiment, a six port valve is used. FIG. 2 schematically illustrates the system (e.g., system 200, or system 100 of FIG. 1) in backflush mode. A backflush gas of the same type as the second carrier gas may be supplied to valve 5 and flows through to vent 31 at nominal flow rate of about 25 mL/min. The second carrier may flow through valve 5 to tee 13 and the gas stream from the water separator 4 flows through valve 5 to the detector system 6. When valve 5 is actuated, the backflush gas may sweep the column effluent and oxygen gas out of vent 31. The second carrier gas may flow to the detector system 6. The backflush valve 5 may be used to divert the unwanted components such as the solvent from the system. Prior to analysis, a small amount of solvent may be injected into the system to determine the time window when the valve 5 needs to be actuated. The system used for backflushing may comprise any suitable arrangement and type of valves. Pneumatically actuated valves of low volume are a suitable alternative.

It may be possible to operate the interface system without an open spilt whereby the gas chromatograph interface system is directly connected to detector system 6. In this embodiment, a passive fluid flow sampling system may be employed. For instance, the system may use sampling valves to selectively introduce aliquots of a known standard or sample into the combustion system. Additionally, the flow of sample to the detector system may be controlled by the system configuration and the pressure drop across the system.

In the case that the system is to be used for $^{15}N$ isotope ratios, an additional furnace may be added to system. During the combustion process, oxides of nitrogen can form which can adversely affect the precision and sensitivity of measurements. Thus, a reduction furnace may be added to reduce the oxides of nitrogen to nitrogen gas. The reduction furnace may be located after the water separator 4 so that the amount of water vapor entering the reduction furnace is minimized. The reduction furnace may comprise of components similar to that for the oxidation furnace except that the catalyst would be 100% copper and the operating temperature would be around 650° C. The system may be operated with any arrangement or device that purifies the gas stream so it is more suitable for the detector.

In some embodiments, a sample is injected along with a hydrogen carrier gas. A valve or pressure regulator may be used to control the flow of hydrogen into the gas chromatograph. Upon exiting the gas chromatograph, the gas may be mixed with a make-up gas (e.g., an inert gas) and oxygen. Valves may be used to control the gas flow rate of the make-up gas and oxygen. To reduce the flow rate of the gas stream (milliliters per minute) to suit the accelerator mass spectrometer system (microliters per minute), the make-up gas may be introduced at a significantly lower flow rate than the flow rate of the hydrogen carrier gas. The gas stream may then enter the combustion system equipped with catalysts to ensure simultaneous and complete combustion of the gas stream. The resulting gas stream from the combustion system may be kept above approximately 100 degrees Celsius before entering the water separator. The water separator uses NAFION® tubing for water vapor removal. The first half of the water separator is wrapped in heated tape, whereas the second half is not heated. The gas stream flows though the tubing, and the tubing is swept with an external flow of a drying gas, such as Argon, at flow rate of up to about 1000 milliliters per minute.

Prior to entering the accelerator mass spectrometer, a backflush gas may be introduced at rate of less than about 30 ml/min.

FIG. 3 depicts a furnace interface and combustion system according to one embodiment of the invention. Interface system 300 may include furnace interface 2 and combustion system 3, of system 100 shown in FIG. 1. Furnace interface 2 comprises tee 14 and heated block 16. Tee 14 may be heated so that compounds are conveyed to reactor tube 15 in the vapor phase. Reactor tube 15 may be held in tee 14 with a ferrule, while capillary 17 may be inserted through the axis of tee 14 into the reactor tube 15. The oxygen and second carrier gas may flow through the annular space between tee 14 and capillary 17 and may merge coaxially with the hydrogen carrier at the end of capillary 17. Tee 14 may be heated by any suitable means such as an aluminum block fitted with a heater cartridge. A thermocouple and a temperature controller are commonly employed for transfer zones in gas chromatographs. In this embodiment, an FID weldment is used as the furnace interface 2. Tee 14 may be located wholly inside the oven of gas chromatograph 1 if the heating supplied is sufficient. Tee 14 may also be located outside of the gas chromatograph 1 if no heating is desired. Tee 14 may be located in a heated zone so that the gas flowing through it are exposed to a constant temperature. Temperature fluctuations cause fluctuations in flow rate of gases which effect the stability and precision of the mass spectrometer. The second carrier gas and oxygen may be supplied by any suitable means.

Combustion system 3 may be configured to convert the compounds of interest into $CO_2$ and $N_2$ (or $SO_2$) gas for isotopic composition measurements and combust the hydrogen carrier gas to water. The compounds may enter reactor tube 15 from furnace interface 2. Combustion system 3 may be comprised of two main components: reactor tube 15 and furnace 20. Reactor tube 15 may comprise high purity about 99.8% alumina ceramic ($Al_2O_3$) and metal catalyst wires 19 inside. Any suitable material may be used for reactor tube 15 including quartz and fused silica.

In one embodiment, reactor tube 15 is approximately 360 mm long so that it extends 20-40 mm from either end of the furnace 20. Reactor tube 15 may be centered along the axis of furnace 20 to ensure even heat distribution and may be held in place by any suitable means. The exit of the of the combustion tube may be connected to water separator 4 by a metal union and ferrules or any suitable method of connection. Reactor tube 15 may be configured to extend far enough from furnace 20 so that the connections at it ends are not exposed to high temperatures and melt.

In one embodiment, capillary column 8 and 17 has an inner diameter of about 0.53 mm so that adequate chromatographic separation can be achieved for compounds containing up to about 10 μg of carbon. In certain embodiments, the sample size required for accelerator mass spectrometer measurements at natural abundances levels is currently at least about 2 micrograms of carbon which precludes the use of smaller columns. Smaller diameter columns may be used when the interface is used with an isotope ratio mass spectrometer as smaller sample size can be analyzed. In certain embodiments, reactor tube 15 has a nominal outer diameter of about 1.57 mm and inner diameter of about 0.79 mm. The catalyst wire 19 may have a diameter of about 0.3 to about 0.4 mm which leaves an annular gap of about 0.4 to about 0.5 mm so as to approximately match the inner diameter of column 8 and 17. This configuration may conserve the laminar flow rate of the gases, avoid blockages and dead volumes, and prevent peak broadening. Other dimensions may be used including a shorter overall length or a smaller inner diameter. The dimensions of reactor tube 15 may be determined by the required capacity of the furnace and diameter of the capillary 8 and 17.

In some embodiments, furnace 20 is an approximately 305 mm long, cylindrical resistively heated ceramic fiber furnace with an inner diameter of about 12.7 mm and an outer diameter of about 50.8 mm. The temperature inside the furnace may be maintained at around 850° C. using temperature controller 21 fitted with a K-type thermocouple. Any suitable heating arrangement can be used which maintains the combustion tube at a constant temperature. Alternatives include an aluminum block fitted with a heater cartridge. In certain embodiments, a compound does not need to combusted prior to analysis and combustion system 3 could be eliminated. In this system, the oxidation of the hydrogen carrier gas could take place in an interface between the GC 1 and water separator 4.

Catalyst wire 19 may comprise copper, nickel and platinum. Three copper, one nickel and one platinum wire with a diameter of about 0.1 mm may be twisted together to give a final total diameter about 0.3 to about 0.4 mm and about 6-8 turns per centimeter. An approximately 25-30 cm length of twisted catalyst wire 19 may be inserted into the combustion tube and may be positioned so that it is located in the heated zone of furnace 20. Capillary column 17 may be positioned so that its exit is close (about 1 to about 5 mm) to catalyst wire 19 and in the heated zone of furnace 20. The gap may be kept small so the mixing zone of gases may be kept small. Any catalysts with a suitable composition or dimension may can be used including a single wire composed of alloyed metals.

Catalyst wire 19 may serves to provide a metal/metal oxide catalyst system for combustion of compounds as they pass though reactor tube 15 during operation. Initially the catalyst wire 19 may be heated to approximately 650° C. overnight in the presence of oxygen produce oxides of the metals. The production of oxides may be achieved by operating gas chromatograph 1 with helium carrier gas and the oxygen supply switched on. The metal/metal oxide may act as both a catalyst and source of oxygen. Copper oxide decomposes at temperatures of around 800° C. and may act independently as a source of oxygen. The partial pressure of oxygen increases with temperature. In contrast from prior art systems (where the catalyst provides the oxygen for a complete analytical run), a constant supply of oxygen gas may be added prior to combustion for the hydrogen carrier gas as well as the compounds. The constant supply of oxygen gas ensures the system has sufficient oxygen for a complete analytical run. During operation, the oxygen supply may be lowered close to the stoichiometric ratio of about 2:1 ($H_2:O_2$) with hydrogen. Decomposition of the copper oxide in catalyst wire 19 may supply additional oxygen as required. A large excess of oxygen may be avoided so as minimize the total flow of gas to detector system 6. Three copper wires may be used to ensure there is sufficient copper oxide. Alternatively, metal oxides can be loaded in the reactor tube 15 and the conditioning step omitted.

In one embodiment, the combustion system has a resistively heated electric furnace with a ceramic alumina combustion tube. The ceramic alumina combustion tube extends and contains a catalyst to ensure complete combustion of the sample. The furnace is approximately 30 cm in length and is operated at approximately 300-850 degrees Celsius. The ceramic alumina tube may be made of high purity alumina (about 99.8%) and is slightly longer than the furnace to permit the attachment of fittings. The ceramic alumina tube has internal diameter of approximately 0.8 mm and is packed with a combustion catalyst. The combustion catalyst is comprised of 3 copper, 1 nickel, and 1 platinum wires of approximately 0.1 mm diameter twisted together as to avoid excessive restriction and permit an adequate gas flow. The combustion catalyst wires are contained within the heated zone of the furnace.

Figure 4:
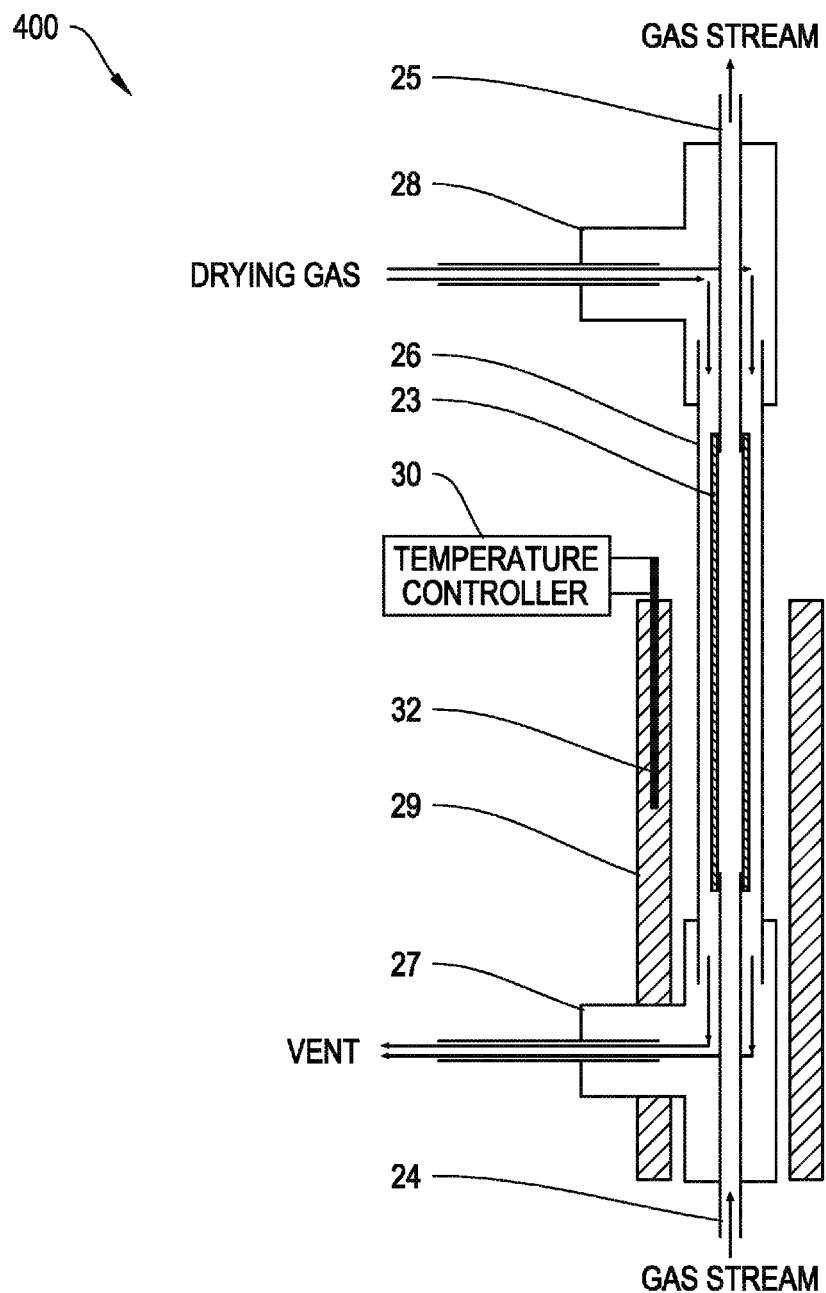
FIG. 4 depicts a water separator of a gas chromatograph-combustion system of FIG. 1, according to an embodiment of the invention.

FIG. 4 depicts a water separator of a gas chromatograph-combustion system of FIG. 1, according to an embodiment of the invention. Water separator 4 (e.g., system 400) may be used to remove water generated during combustion from the gas stream. In certain embodiments, the water separator 4 is configured to lower the water vapor in the gas stream to around 1 part per million by volume (ppmv). The gas stream may pass through capillary membrane 23 that selectively removes water while leaving $CO_2$ and $N_2$ unchanged. In one embodiment, the membrane used in this system is an ionomeric NAFION tubing manufactured by Permapure, Toms River, N.J., USA. However, any suitable material may be used. NAFION is a sulfonated tetrafluoroethylene based fluoropolymer-copolymer that selectively removes water via an ion exchange process. In one embodiment, the water separator 4 includes a 325 mm length of 6.35 mm o.d. quartz tubing fitted with two tees.

An approximately 26 cm length of NAFION tubing 23 may be shrink fitted onto two lengths of fused silica capillary 24, 25. In one embodiment, the I.D. of the NAFION tubing 23 is approximately 0.356 mm and the O.D. of the fused silica capillary 24, 25 is nominally 0.36 mm. Fused silica capillary 24 and fused silica capillary 25 may act as connecting tubing and their I.D. may be dependent on the desired flow rate of the gas stream through the system. In this embodiment, system, capillary tubing with an I.D. of about 0.43 mm is for the entrance end 24 and about 0.25 mm may be used on the exit end 25. Shrink fitting may be achieved by expanding the end (~0.5 cm) of the NAFION tubing 23 in methanol, sliding it over the end of Fused silica capillary 24 and fused silica capillary 25 and evaporating the methanol with a stream of air. Shrink fitting may form a seal that is gas tight. Any appropriate adhesive may also be used. NAFION tubing 23 may be held in a tubular housing that is constructed nominally from a 30 cm length of about 6.35 mm glass tubing 26 fitted with tee 27 and tee 28 at each end. Ferrules may hold the glass tube and capillaries in place. The I.D. of the glass tubing is nominally 4 mm.

A drying gas may be admitted at the side port of tee 28 at a nominal flow rate of about 500 mL/min. Argon and helium are suitable drying gases however, other gases including air maybe used. The flow rate of the drying gas may be controlled by a needle valve. The drying gas may pass through the annular space of water separator 4, exiting at the side port of lower tee 27. This configuration may ensure the driest gas is present at exit end of the water separator 4. In one embodiment, as the gas stream passes through NAFION tubing 23, water diffuses through the membrane and is swept away counter currently by the drying gas. The drying gas may determine the final water content of the gas stream. Prior to admission, the drying gas may be passed through a trap that contains a desiccant such as molecular sieves.

The entrance end of water separator 4 may be heated with heater tape 29 that is controlled with temperature controller 30 fitted with a K-type thermocouple 32. Heater tape 29 may be about 12.7 mm wide and about 1.2 m long and double wrapped over the lower half of water separator 4. Thermocouple 32 may be positioned between the two layers of heater tape 29. NAFION tubing 23 may be positioned so that the length in the heated zone is maximized. Water separator 4 may be operated at around 110° C. to prevent water vapor from condensing. NAFION tubing 23 may be re-tensioned as the water separator 4 warms up to compensate for relaxation and softening. The length of fused silica capillary 24 and fused silica capillary 25 may be kept to a minimum to minimize peak broadening and back pressure. The dimensions of water separator 4 components and methods of connection may be altered to suit the capacity and performance as desired. The operating temperature may be altered, and at lower hydrogen carrier gas flows, the heating may be removed altogether.

Water separator 4 may be operated in such a configuration to maximize water removal capacity while minimizing the residual water vapor in the gas stream that is transmitted to the ion source. Water separator 4 may be partially heated to increase its water removal capacity. NAFION membrane 23 may diffuse water by ion exchange. By sweeping away water at the external surface with a drying gas, a partial pressure gradient may form, driving the preevaporation process for inside to out. The rate of water adsorption is temperature dependent and may be increased with heating. Heating may be important in this system as large flow rates of water vapor generated from combustion of the hydrogen carrier gas must be removed.

The exit end of water separator 4 may be operated at room temperature or cooler to minimize the residual water vapor in the gas stream. Residual water vapor is detrimental to the performance of the mass spectrometer. Specifically, in an isotope ratio mass spectrometer ion source it may cause proton transfer reactions that result in an interference at about m/z 45 Da due to the formation of $HCO_2^+$. In an accelerator mass spectrometer fitted with a microwave ion source it may cause electrical break-downs. The operating temperature of water separator 4 and dryness of the drying gas may determine the final equilibrium dew point of the membrane and gas stream. Gas at room temperature that has been passed through a trap containing molecular sieves may be used in this system. Other types of traps such as a liquid nitrogen trap could be used to cryogenically remove residual water from the gas stream. A liquid nitrogen trap can only be used after the bulk of the water vapor has been removed first by a water separator 4.

In certain embodiments, water separator may comprise an approximately 26 cm length of NAFION® tubing with an internal diameter of approximately 0.6 mm, wherein the tubing is held in a housing. The NAFION® tubing has an internal diameter similar to that of the chromatograph column and combustion system as to avoid excessive restriction and permit an adequate gas flow. Water separator 4 may be configured such that the front part is wrapped with heating tape, wherein the heating tape is heated up to about 150 degrees Celsius to maximize water vapor removal while the back part is at ambient temperature or cooled to minimize residual water vapor in the gas stream. Electronic temperature controllers and thermocouples may be used to heat the furnace and water separator and maintain them at a constant temperature. Thermocouples may be made of a suitable material such as a K-type thermocouple (chromel-alumel). In certain embodiments, the NAFION tubing may not need to be heated, such as when used in conjunction with an IRMS for identifying $^{15}N$ stable isotopes.

Figure 5:
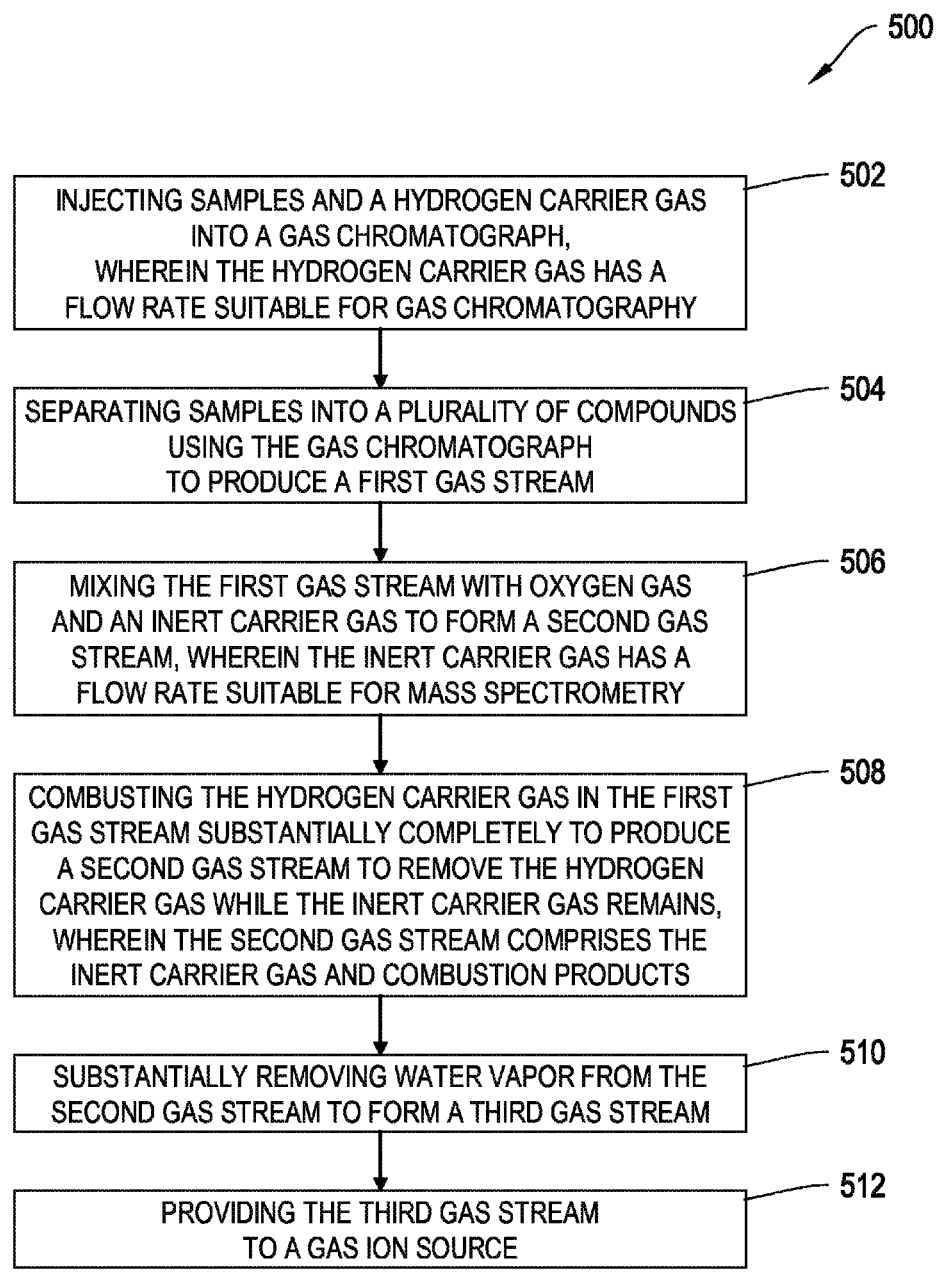
FIG. 5 is a flow chart depicting a process for analyzing a sample, according to an illustrative embodiment of the invention.

FIG. 5 is a flow chart depicting an illustrative process for analyzing a sample, according to an embodiment of the invention. At step 502 of process 500, samples and a hydrogen carrier gas may be injected into a gas chromatograph. The samples may be an organic sample. The sample of interest may be analyzed for its isotopic composition. As discussed in relation to FIG. 1, hydrogen carrier gas is a suitable gas for carrying the sample through a gas chromatograph. Other methods for separating samples into discrete components may be used. If a sample has already been purified, a gas chromatograph may not be needed. The system and method for injection are discussed at length in relation to gas chromatograph 1 in FIG. 1.

At step 504, the samples may be separated into a plurality of compounds to produce an output gas stream from the gas chromatograph. The method and system for separating compounds using a gas chromatograph are discussed in relation to FIG. 1.

At step 506, the output gas stream from the gas chromatograph with oxygen gas and an inert carrier gas suitable for a mass spectrometer may be mixed to produce an input gas stream for the combustion system. In some embodiments, mixing the output gas stream from the gas chromatograph with oxygen gas comprises providing an amount of oxygen gas at substantially the stoiciometric ratio of 2:1 with the hydrogen carrier gas to allow for combustion to occur substantially completely. The inert carrier gas may be helium gas or argon gas or any suitable carrier gas for mass spectrometry. The system and method for mixing oxygen gas and inert carrier gas are discussed in relation to FIGS. 1 and 3.

At step 508, the hydrogen carrier gas in the input gas stream of the combustion system may be combusted substantially completely to produce an output gas stream for the combustion system. The output gas stream of the combustion system may include the inert carrier gas, carbon dioxide gas, and water vapor. Combusting the hydrogen carrier gas in the input gas stream of the combustion system may comprise using metal and metal oxides as a catalyst. In some embodiments, the output gas stream of the combustion system further includes nitrogen gas, and the gas stream for analysis further includes nitrogen gas. The output gas stream of the combustion system may further include nitrogen oxide, and the gas stream for analysis further includes nitrogen oxide. The method and system for combustion are discussed at length in relation to FIGS. 1 and 3.

At step 510, the water vapor from the output gas stream of the combustion system may be substantially removed using a water separator to produce a gas stream for analysis. The gas stream for analysis may comprise inert carrier gas and carbon dioxide gas. The method and system for water removal are discussed in relation to FIGS. 1 and 4.

At step 512, the gas stream for analysis may be provided to the mass spectrometer fitted with a gas ion source. In some embodiments, the analysis is isotope ratio mass spectrometry analysis. In some other embodiments, the analysis is accelerator mass spectrometry analysis. The method and system for providing the gas stream are discussed in relation to FIGS. 1 and 2.

In certain embodiments, process 500 further comprises substantially removing nitrogen oxide in the gas stream for analysis in a reduction furnace to reduce nitrogen oxide into nitrogen gas. If $^{15}N$ isotope ratio analysis is desired, it may be desirable to use an additional furnace to remove nitrogen oxide that may have been produced by the combustion system. Further details regarding the additional reduction furnace are discussed in relation to FIG. 1.

Figure 6:
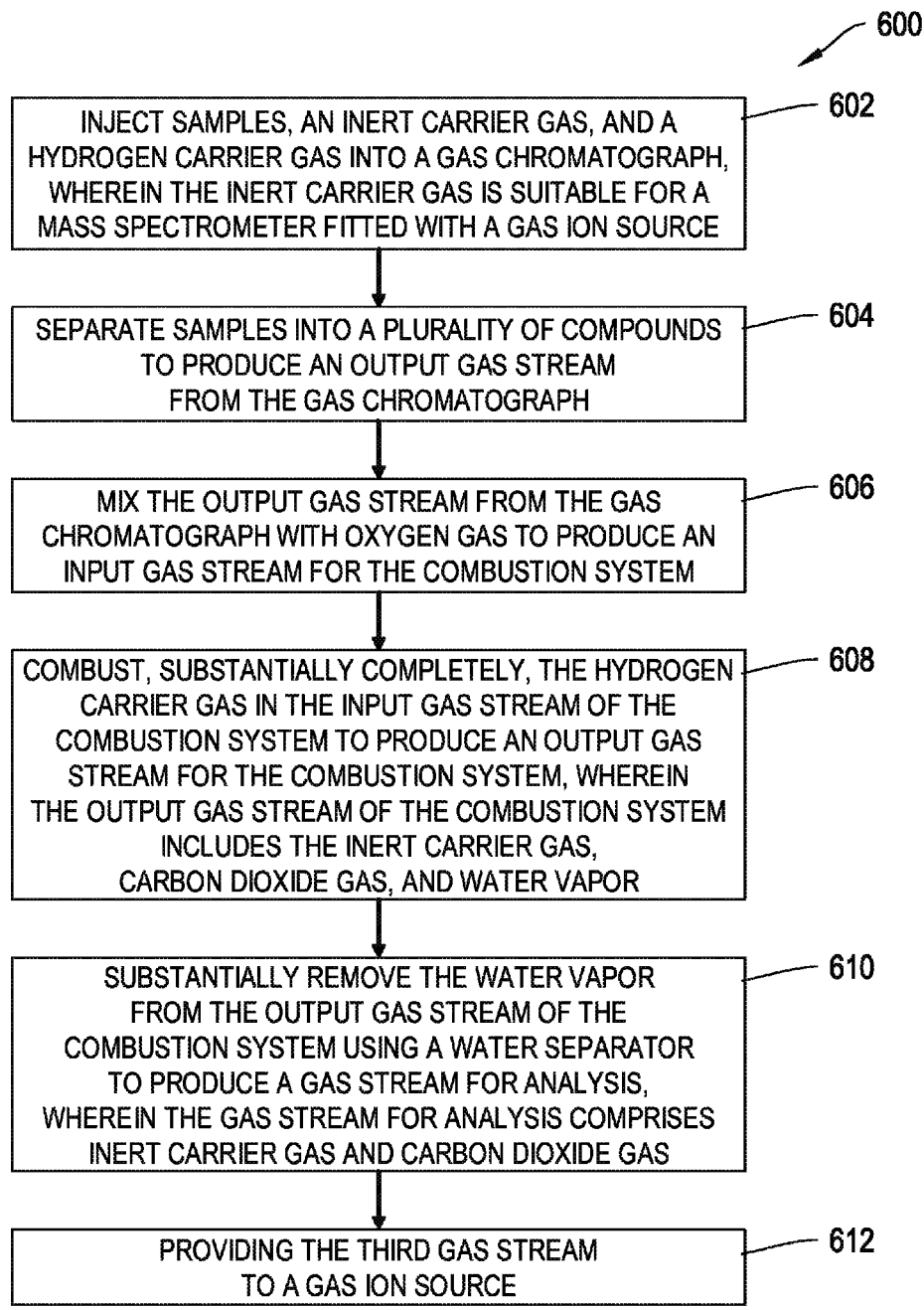
FIG. 6 is a flow chart depicting a process for analyzing a sample, according to an illustrative embodiment of the invention.

FIG. 6 is a flow chart depicting another illustrative process for analyzing a sample, according to an embodiment of the invention. Process 600 simplifies process 500 by introducing the inert carrier gas at the gas chromatograph instead of at combustion system. Details regarding various steps are discussed in relation to FIGS. 1 through 5. At step 602 of process 600, samples, an inert carrier gas, and a hydrogen carrier gas may be injected into a gas chromatograph. The inert carrier gas may be suitable for a mass spectrometer fitted with a gas ion source. In one embodiment, 10% helium and 90% hydrogen may be injected into the gas chromatograph. In another embodiment, the two separate gas supplies may be mixed at a tee before introducing them to the gas chromatograph.

At step 604, samples may be separated into a plurality of compounds to produce an output gas stream from the gas chromatograph. The system and method for separating samples into discrete compounds are discussed in relation to gas chromatograph 1 in FIG. 1.

At step 606, the output gas stream from the gas chromatograph may be mixed with oxygen gas to produce an input gas stream for the combustion system. The method and system for mixing the output gas stream with oxygen gas are discussed in relation to FIGS. 1 and 3.

At step 608, the hydrogen carrier gas in the input gas stream gas stream of the combustion system may be combusted substantially to produce an output gas stream for the combustion system. The output gas stream of the combustion system may include the inert carrier gas, carbon dioxide gas, and water vapor. The systems and method for combustion are discussed in relation to FIGS. 1 and 3.

At step 610, the water vapor from the output gas stream of the combustion system may be substantially removed using a water separator to produce a gas stream for analysis, wherein the gas stream for analysis comprises inert carrier gas and carbon dioxide gas. The method and system for water removal are discussed at length in relation to FIGS. 1 and 4.

At step 612, the gas stream for analysis may be provided to the mass spectrometer fitted with a gas ion source. The method and system for providing the gas stream is discussed at length in relation to FIGS. 1 and 2.

Figure 7:
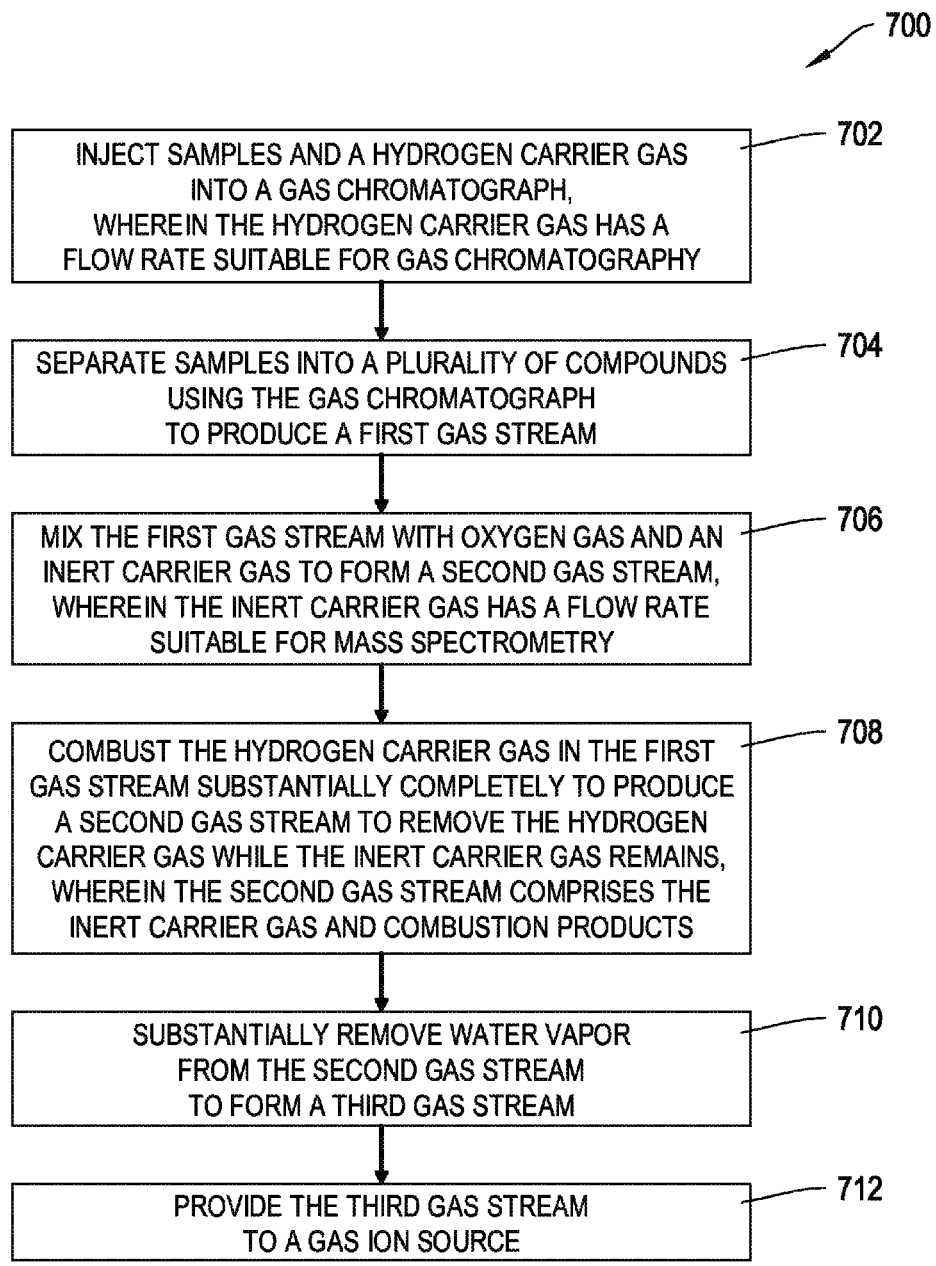
FIG. 7 is a flow chart depicting a process for interfacing a gas chromatograph with a mass spectrometer, according to an illustrative embodiment of the invention.

FIG. 7 is a flow chart depicting an illustrative process for interfacing a gas chromatograph with a mass spectrometer, according to an embodiment of the invention. At step 702 of process 700, samples and a hydrogen carrier gas may be injected into a gas chromatograph, wherein the hydrogen carrier gas has a flow rate suitable for gas chromatography. In some embodiments, the flow rate suitable for gas chromatography is about 1.0 to about 10 milliliters per minute. In other embodiments, the flow rate suitable for gas chromatography is about 1.0 to about 100 milliliters per minute. The method and system for injecting samples and hydrogen carrier is discussed at length in relation to FIG. 1.

At step 704, samples into a plurality of compounds may be separated using the gas chromatograph to produce a first gas stream.

At step 706, the first gas stream may be mixed with oxygen gas and an inert carrier gas to form a second gas stream. The inert carrier gas may have a flow rate suitable for mass spectrometry. In some embodiments, the flow rate suitable for mass spectrometry is about 0.001 to about 1.0 milliliters per minute. In some embodiments, the flow rate suitable for mass spectrometry is about 0.2 to about 1.0 milliliters per minute. Discussion of flow rate limitations, system and method for mixing the first gas stream with oxygen gas and an inert carrier gas are discussed in relation to FIG. 1.

At step 708, the hydrogen carrier gas in the first gas stream may be combusted substantially completely to produce a second gas stream to remove the hydrogen carrier gas while the inert carrier gas remains. The second gas stream may comprise the inert carrier gas and combustion products. The method and system for combustion are discussed at length in relation to FIGS. 1 and 3.

At step 710, water vapor may be removed from the second gas stream to form a third gas stream. The method and system for water removal are discussed at length in relation to FIGS. 1 and 4.

At step 712, the third gas stream may be provided to a gas ion source. In some embodiments, the gas ion source is a microwave plasma ion source. Gas ion sources, method and system for providing the third gas stream to a gas ion source are discussed at length in relation to FIG. 1. The third gas stream may be provided to a gas ion source for ionization such that it may be analyzed by a mass spectrometer.

Figure 8:
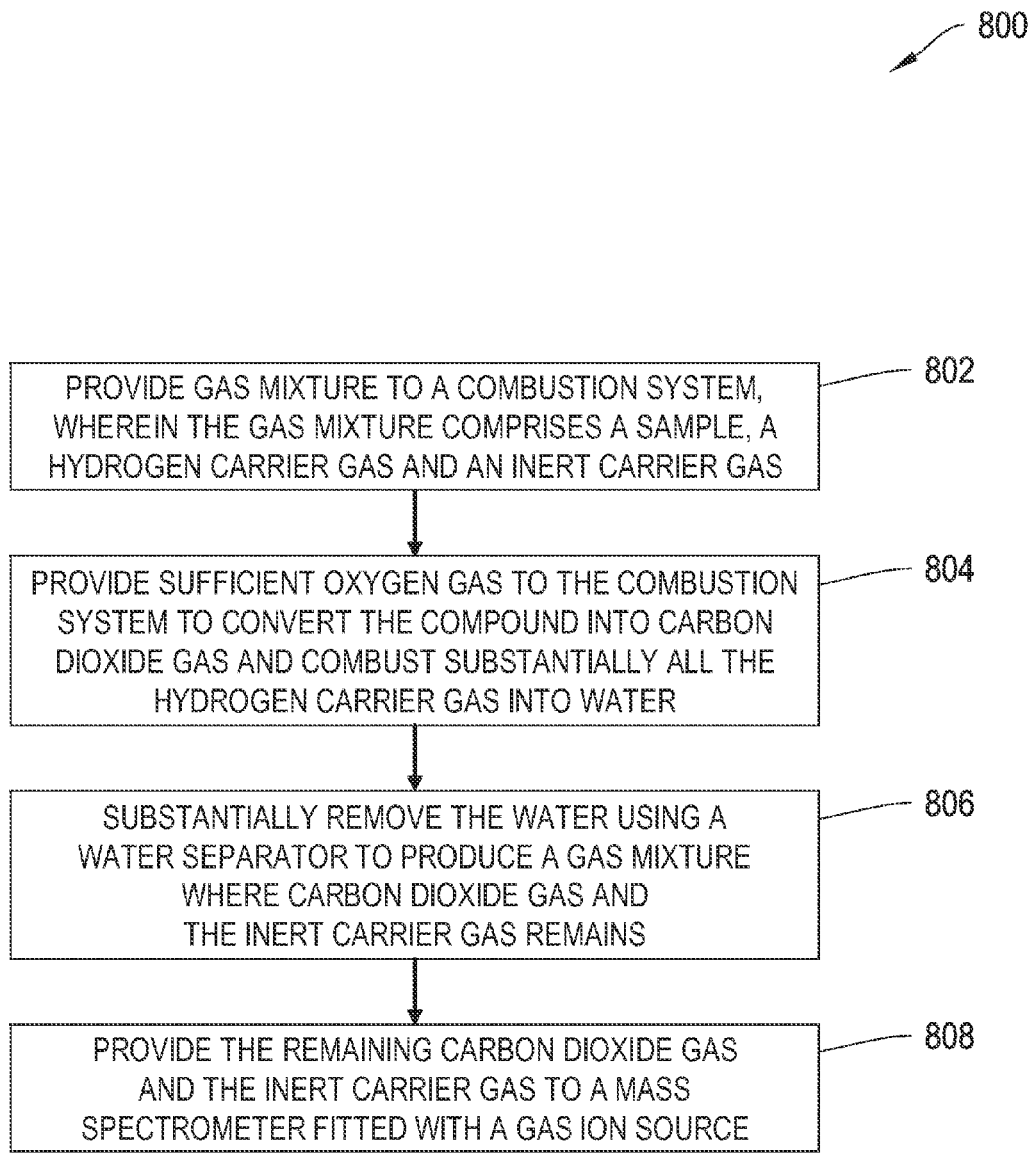
FIG. 8 is a flow chart depicting a process for preparing a sample for mass spectrometry, according to an illustrative embodiment of the invention.

FIG. 8 is a flow chart depicting an illustrative process for preparing a sample for mass spectrometry, according to an embodiment of the invention. At step 802 of process 800, gas mixture may be provided to a combustion system. The gas mixture may comprise a sample, a hydrogen carrier gas and an inert carrier gas. The method and system for combustion are discussed at length in relation to FIGS. 1 and 3.

At step 804, sufficient oxygen gas may be provided to the combustion system to convert the compound into carbon dioxide gas and combust substantially all the hydrogen carrier gas into water. The method and system for providing oxygen gas are discussed at length in relation to FIGS. 1 and 3.

At step 806, the water may be substantially removed using a water separator to produce a gas mixture where carbon dioxide gas and the inert carrier gas remains. The method and system for water removal are discussed at length in relation to FIGS. 1 and 4.

At step 808, the remaining carbon dioxide gas and the inert carrier gas may be provided to a mass spectrometer fitted with a gas ion source. The method and system for providing the remaining carbon dioxide gas and the inert carrier gas are discussed at length in relation to FIG. 1.

Figure 9:
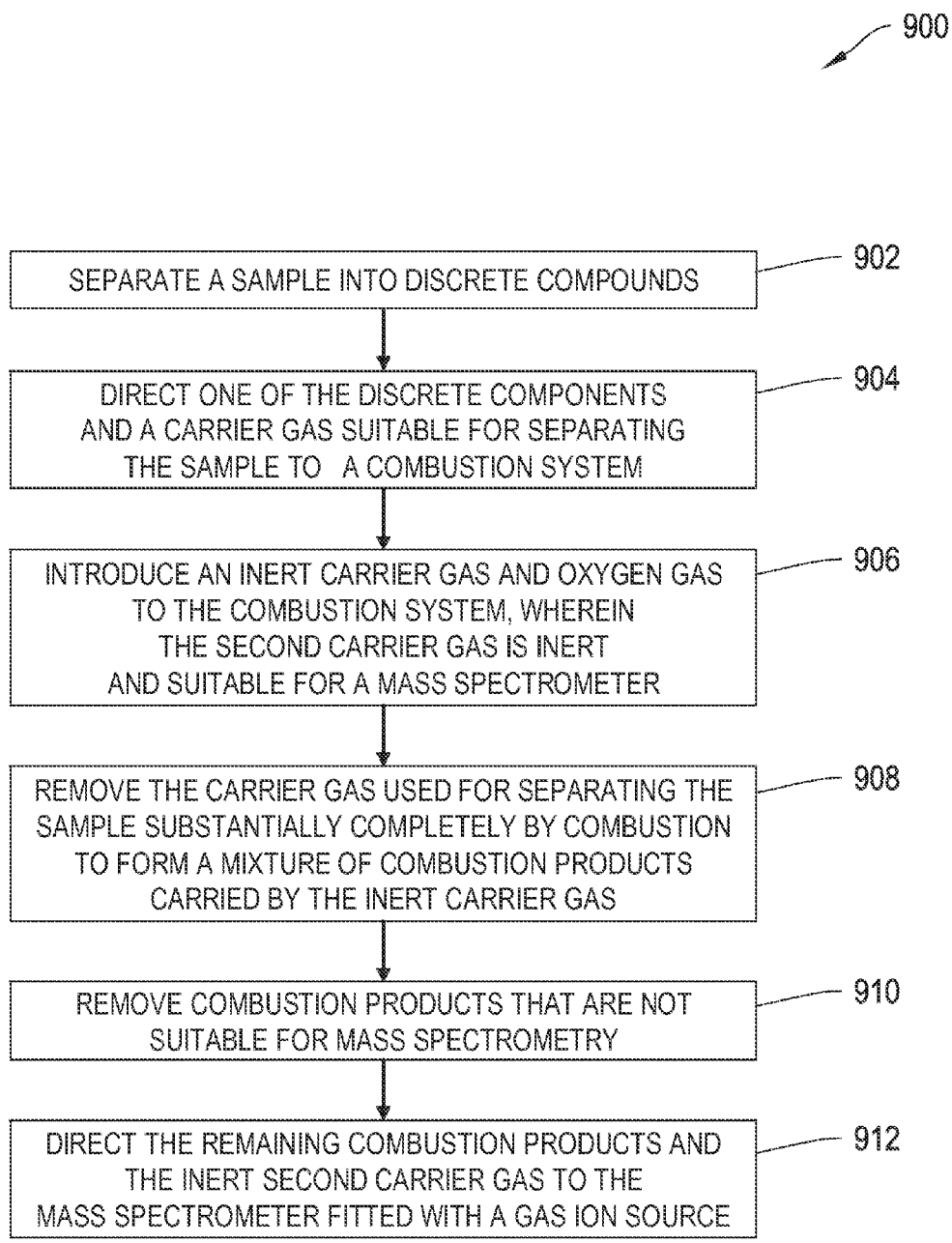
FIG. 9 is a flow chart depicting a process for analyzing a sample, according to an illustrative embodiment of the invention.

FIG. 9 is a flow chart depicting an illustrative process analyzing a sample in an online system, according to an embodiment of the invention. At step 902 of process 900, a sample may be separated into discrete compounds or discrete components. In some embodiments, separating the sample into discrete compounds comprises mixing a sample with a carrier gas suitable for separating the sample and providing the sample and the carrier gas suitable for separating the sample to a gas chromatograph to separate the sample into discrete components. The method and system for separating samples is discussed at length in relation to gas chromatograph 1 of FIG. 1.

At step 904, one of the discrete components and a carrier gas suitable for separating the sample may be directed to a combustion system. The method and system for directing the discrete components to a combustion system are discussed in relation to furnace interface 2 and combustion system 3 of FIGS. 1 and 3.

At step 906, an inert carrier gas and oxygen gas may be introduced to the combustion system. The second carrier gas may be inert and may be suitable for a mass spectrometer. The method and system for introducing the inert carrier gas and oxygen gas are discussed in relation to furnace interface 2 of FIGS. 1 and 3.

At step 908, the carrier gas used for separating the sample may be removed substantially completely by combustion to form a mixture of combustion products carried by the inert carrier gas. In some embodiments, combustion products include carbon dioxide gas and water vapor. The method and system for combustion are discussed at length in relation to combustion system 3 of FIGS. 1 and 3.

At step 910, combustion products that are not suitable for mass spectrometry may be removed. In some embodiments, water vapor generated from the combustion using a water separator. The method and system for water vapor removal are discussed in relation to water separator 4 of FIGS. 1 and 4.

At step 912, the remaining combustion products and the inert second carrier gas may be directed to the mass spectrometer fitted with a gas ion source. The method and system for step 912 are discussed in relation to FIGS. 1 and 2.

Those skilled in the art will know or be able to ascertain using no more than routine experimentation, many equivalents to the embodiments and practices described herein. Variations, modifications, and other implementations of what is described, including, but not limited to temperature ranges, flow rates, component sizes and makes, and any other operating conditions, may be employed without departing from the spirit and scope of the invention. More specifically, any of the method and system features described above or incorporated by reference may be combined with any other suitable method or system feature disclosed herein or incorporated by reference, and is within the scope of the contemplated inventions. The systems and methods may be embodied in other specific forms without departing from the spirit or essential characteristics thereof. The foregoing embodiments are therefore to be considered in all respects illustrative, rather than limiting of the invention. The teachings of all references cited herein are hereby incorporated by reference in their entirety.

What is claimed is:

1. A method for analyzing a sample, comprising:
   injecting samples and a hydrogen carrier gas into a gas chromatograph;
   separating samples into a plurality of compounds to produce an output gas stream from the gas chromatograph;
   mixing the output gas stream from the gas chromatograph with oxygen gas and an inert carrier gas suitable for a mass spectrometer to produce an input gas stream for a combustion system;
   combusting, substantially completely, the hydrogen carrier gas in the input gas stream of the combustion system to produce an output gas stream from the combustion system, wherein the output gas stream of the combustion system includes the inert carrier gas, carbon dioxide gas, and water vapor;
   substantially removing the water vapor from the output gas stream of the combustion system using a water separator to produce a gas stream for analysis, wherein the gas stream for analysis comprises the inert carrier gas and the carbon dioxide gas; and
   providing the gas stream for analysis to the mass spectrometer fitted with a gas ion source.

2. The method in claim 1, wherein the mass spectrometer includes at least one of an isotope ratio mass spectrometer and an accelerator mass spectrometer.

3. The method in claim 1, wherein mixing the output gas stream from the gas chromatograph with oxygen gas comprises:
   providing an amount of oxygen gas at substantially the stoiciometric ratio of 2:1 with the hydrogen carrier gas to allow for combustion to occur substantially completely.

4. The method in claim 1, wherein combusting at least one of the hydrogen carrier gas and the sample in the input gas stream of the combustion system comprises using metal and metal oxides as a catalyst.

5. The method in claim 1, wherein the output gas stream of the combustion system further includes nitrogen gas, and the gas stream for analysis further includes nitrogen gas.

6. The method in claim 5, wherein the output gas stream of the combustion system further includes oxides of nitrogen, and the gas stream for analysis further includes oxides of nitrogen.

7. The method in claim 5, further comprises:
substantially removing nitrogen oxide in the gas stream for analysis in a reduction furnace to reduce nitrogen oxide into nitrogen gas.

8. The method in claim 1, wherein the inert carrier gas is helium gas or argon gas.

9. The method of claim 1, wherein separating samples into a plurality of compounds includes separating into a one or more components, each component having one or more compounds.

10. A method for analyzing a sample, comprising:
injecting samples, an inert carrier gas, and a hydrogen carrier gas into a gas chromatograph, wherein the inert carrier gas is suitable for a mass spectrometer fitted with a gas ion source;
separating samples into a plurality of compounds to produce an output gas stream from the gas chromatograph;
mixing the output gas stream from the gas chromatograph with oxygen gas to produce an input gas stream for a combustion system;
combusting, substantially completely, the hydrogen carrier gas in the input gas stream of the combustion system to produce an output gas stream from the combustion system, wherein the output gas stream from the combustion system includes the inert carrier gas, carbon dioxide gas, and water vapor;
substantially removing the water vapor from the output gas stream of the combustion system using a water separator to produce a gas stream for analysis, wherein the gas stream for analysis comprises the inert carrier gas and the carbon dioxide gas; and
providing the gas stream for analysis to the mass spectrometer fitted with the gas ion source.

11. The method of claim 10, wherein separating samples into a plurality of compounds includes separating into a one or more components, each component having one or more compounds.

12. A method for interfacing a gas chromatograph with a mass spectrometer, comprising:
injecting samples and a hydrogen carrier gas into a gas chromatograph, wherein the hydrogen carrier gas has a flow rate suitable for gas chromatography;
separating samples into a plurality of compounds using the gas chromatograph to produce a first gas stream;
mixing the first gas stream with oxygen gas and an inert carrier gas to form a second gas stream, wherein the inert carrier gas has a flow rate suitable for mass spectrometry;
combusting the hydrogen carrier gas in the second gas stream substantially completely to produce a third gas stream, wherein combusting the second gas stream removes the hydrogen carrier gas while the inert carrier gas remains, and wherein the third gas stream comprises the inert carrier gas and combustion products;
substantially removing water vapor from the third gas stream to form a fourth gas stream; and
providing the fourth gas stream to a gas ion source fitted to the mass spectrometer.

13. The method in claim 12, wherein the flow rate suitable for gas chromatography is about 1 to about 100 milliliters per minute.

14. The method in claim 12, wherein the flow rate suitable for mass spectrometry is about 0.001 to about 1.0 milliliters per minute.

15. The method in claim 12, wherein the gas ion source is at least one of a microwave plasma ion source and an electron ionization source.

16. The method of claim 12, wherein separating samples into a plurality of compounds includes separating into one or more components, each component having one or more compounds.

* * * * *